US006773402B2

(12) United States Patent
Govari et al.

(10) Patent No.: US 6,773,402 B2
(45) Date of Patent: Aug. 10, 2004

(54) LOCATION SENSING WITH REAL-TIME ULTRASOUND IMAGING

(75) Inventors: Assaf Govari, Haifa (IL); Ilya Beletsky, Jerusalem (IL)

(73) Assignee: Biosense, Inc., New Brunswick, NJ (US)

(*) Notice: Subject to any disclaimer, the term of this patent is extended or adjusted under 35 U.S.C. 154(b) by 14 days.

(21) Appl. No.: 10/078,746

(22) Filed: Feb. 19, 2002

(65) Prior Publication Data

US 2003/0013958 A1 Jan. 16, 2003

Related U.S. Application Data

(63) Continuation-in-part of application No. 09/902,087, filed on Jul. 10, 2001.

(51) Int. Cl.[7] ................................................. A61B 8/02
(52) U.S. Cl. .................... 600/459; 600/437; 600/443; 600/462; 600/466
(58) Field of Search ............................ 600/437–472

(56) References Cited

U.S. PATENT DOCUMENTS

| | | | | |
|---|---|---|---|---|
| 4,821,731 A | * | 4/1989 | Martinelli et al. .......... | 600/463 |
| 4,841,977 A | * | 6/1989 | Griffith et al. .............. | 600/439 |
| 5,078,148 A | * | 1/1992 | Nassi et al. .................. | 600/455 |
| 5,243,988 A | * | 9/1993 | Sieben et al. ............... | 600/463 |
| 5,391,199 A | | 2/1995 | Ben-Haim | |
| 5,398,691 A | | 3/1995 | Martin et al. | |
| 5,443,489 A | | 8/1995 | Ben-Haim | |
| 5,577,502 A | | 11/1996 | Darrow et al. | |
| 5,588,432 A | * | 12/1996 | Crowley ...................... | 600/439 |
| 5,680,860 A | * | 10/1997 | Imran ........................... | 600/374 |
| 5,730,129 A | | 3/1998 | Darrow et al. | |
| 5,738,096 A | | 4/1998 | Ben-Haim | |
| 5,797,849 A | | 8/1998 | Vesely et al. | |
| 5,846,205 A | | 12/1998 | Curley et al. | |
| 5,848,969 A | | 12/1998 | Panescu et al. | |
| 5,876,345 A | | 3/1999 | Eaton et al. | |
| 5,904,651 A | | 5/1999 | Swanson et al. | |
| 6,004,269 A | | 12/1999 | Crowley et al. | |
| 6,059,731 A | | 5/2000 | Seward et al. | |
| 6,066,096 A | | 5/2000 | Smith et al. | |
| 6,086,532 A | * | 7/2000 | Panescu et al. ............. | 600/437 |
| 6,095,976 A | | 8/2000 | Nachtomy et al. | |
| 6,120,453 A | | 9/2000 | Sharp | |
| 6,228,032 B1 | | 5/2001 | Eaton et al. | |

FOREIGN PATENT DOCUMENTS

| | | |
|---|---|---|
| CA | 2 355 424 | 2/2002 |
| EP | 945 104 A1 | 9/1999 |
| EP | 0 961 135 A1 | 12/1999 |
| EP | 0 974 936 A2 | 1/2000 |
| GB | 2329708 A | 3/1999 |
| JP | 9-285465 A2 | 11/1997 |
| WO | WO 94/04938 AJ | 3/1994 |
| WO | WO 95 01751 A | 1/1995 |
| WO | WO 96/05768 A1 | 2/1996 |
| WO | WO 97 44089 A | 11/1997 |
| WO | WO 98/18388 A1 | 5/1998 |
| WO | WO 98/46139 A1 | 10/1998 |
| WO | WO 99/55233 A1 | 11/1999 |
| WO | WO 99/58055 A1 | 11/1999 |
| WO | WO 00/19908 A1 | 4/2000 |
| WO | WO 00 23125 A | 4/2000 |

OTHER PUBLICATIONS

Partial European Search Report from correspdoning EP 01 30 6998 dated Dec. 10, 2001.

\* cited by examiner

*Primary Examiner*—Dennis W. Ruhl
*Assistant Examiner*—William C. Jung
(74) *Attorney, Agent, or Firm*—Louis J. Capezzuto

(57) ABSTRACT

Apparatus for mapping a surface of a cavity within a body of a subject includes an elongate probe, having a longitudinal axis and including a distal portion adapted for insertion into the cavity. A primary acoustic transducer on the distal portion of the probe is adapted to emit acoustic waves while the probe is in the cavity. A plurality of secondary acoustic transducers, distributed along the longitudinal axis over the distal portion of the probe, are adapted to receive the acoustic waves after reflection of the waves from the surface of the cavity and to generate, responsive to the received waves, electrical signals indicative of times of flight of the waves.

44 Claims, 5 Drawing Sheets

LOCATION SENSING WITH REAL-TIME ULTRASOUND IMAGING

CROSS-REFERENCES TO RELATED APPLICATIONS

This application is a continuation-in-part of U.S. patent application Ser. No. 09/902,087, filed Jul. 10, 2001, entitled, "Three-dimensional reconstruction using ultrasound," which is assigned to the assignee of the present patent application and is incorporated herein by reference.

FIELD OF THE INVENTION

The present invention relates generally to systems and methods for three-dimensional mapping and reconstruction, and specifically to mapping and reconstruction of the interior of body organs, such as the heart.

BACKGROUND OF THE INVENTION

Methods for three-dimensional geometrical mapping and reconstruction of the endocardial surface are known in the art. For example, U.S. Pat. No. 5,738,096, whose disclosure is incorporated herein by reference, describes methods for mapping the endocardium based on bringing a probe into contact with multiple locations on a wall of the heart, and determining position coordinates of the probe at each of the locations. The position coordinates are combined to form a map of at least a portion of the heart. These methods are effective and accurate, but they require substantial time and skill to carry them out.

PCT Patent Publications WO 99/05971 and WO 00/07501 to Willis et al., which are incorporated herein by reference, describe the use of ultrasound transducers on a reference catheter to locate ultrasound transducers on other catheters (e.g., mapping or ablation catheters) which are brought into contact with the endocardium.

A variety of methods have been developed for non-contact reconstruction of the endocardial surface using intracardial ultrasonic imaging. These methods typically use a catheter with a built-in, miniaturized ultrasonic imaging array or scanner. For example, PCT Patent Publication WO 00/19908, whose disclosure is incorporated herein by reference, describes a steerable transducer array for intracardial ultrasonic imaging. The array forms an ultrasonic beam, which is steered in a desired direction by an active aperture. Similarly, U.S. Pat. No. 6,004,269, whose disclosure is also incorporated herein by reference, describes an acoustic imaging system based on an ultrasound device that is incorporated into a catheter. The ultrasound device directs ultrasonic signals toward an internal structure in the heart to create an ultrasonic image.

Further examples of intracardial ultrasonic imaging are presented in U.S. Pat. No. 5,848,969 and in PCT Patent Publication WO 98/18388, whose disclosures are incorporated herein by reference. These publications describe systems and methods for visualizing interior tissue regions using expandable imaging structures. The structures assume an expanded geometry once inside the heart, which stabilizes an associated imaging probe or array.

U.S. Pat. No. 5,797,849 and PCT Patent Publication WO 99/58055, whose disclosures are also incorporated herein by reference, describe methods for carrying out medical procedures using a three-dimensional tracking and imaging system. The position of a catheter or other probe inside the body is tracked, and its location relative to its immediate surroundings is displayed to improve a physician's ability to precisely position it. Various procedures using such a probe are described in these publications. One such procedure is ultrasonic imaging, using an ultrasound imaging head with transducers held outside the body to image an area inside the body in which a probe with a position sensor is located.

Various methods are known in the art for enhancing ultrasonic images and for extracting information, such as three-dimensional contours, from such images. These methods typically combine information from multiple two-dimensional images to define three-dimensional features. For example, PCT Patent Publication WO 99/55233, whose disclosure is incorporated herein by reference, describes a method for defining a three-dimensional surface of at least a portion of a patient's heart using a plurality of images in different planes. The images are made using an ultrasound transducer at known positions and orientations outside the patient's body. Anatomical landmarks are manually identified in the plurality of images.

Other methods of contour extraction and three-dimensional modeling using ultrasonic images are described in European Patent Application EP 0 961 135 and in Japanese Patent Application JP 9-285465, whose disclosures are also incorporated herein by reference. As another example, PCT Patent Publication WO 98/46139, whose disclosure is incorporated herein by reference, describes a method for combining Doppler and B-mode ultrasonic image signals into a single image using a modulated non-linear mapping function.

U.S. Pat. No. 5,846,205 to Curley et al., which is incorporated herein by reference, describes a phased-array ultrasonic transducer assembly mounted on a catheter. An end portion is attached to the catheter around a transducer array, and the end portion defines an acoustic window which is essentially non-focusing to ultrasonic energy passing therethrough. Because the acoustic window is non-focusing, a relatively small radius of curvature can be used on the radially outer surface of this window.

U.S. Pat. No. 6,066,096 to Smith et al., which is incorporated herein by reference, describes imaging probes and catheters for volumetric intraluminal ultrasound imaging. Apparatus configured to be placed inside a patient includes an elongated body having proximal and distal ends, with an ultrasonic transducer phased array connected to and positioned on the distal end of the elongated body. The ultrasonic transducer phased array is positioned to emit and receive ultrasonic energy for volumetric forward scanning from the distal end of the elongated body. The ultrasonic transducer phased array includes a plurality of sites occupied by ultrasonic transducer elements. At least one ultrasonic transducer element is absent from at least one of the sites, thereby defining an interstitial site. A tool is positioned at the interstitial site. In particular, the tool can be a fiber optic lead, a suction tool, a guide wire, an electrophysiological electrode, or an ablation electrode.

U.S. Pat. No. 6,059,731 to Seward et al., which is incorporated herein by reference, describes a simultaneous side-and-end viewing ultrasound imaging catheter system which includes at least one side array and at least one end array. Each of the arrays has at least one row of ultrasonic transducer elements. The elements are operable as a single ultrasound transducer which are phased to produce different views.

U.S. Pat. No. 5,904,651 to Swanson et al., which is incorporated herein by reference, describes a catheter tube which carries an imaging element for visualizing tissue. The catheter tube also carries a support structure, which extends beyond the imaging element for contacting surrounding tissue away from the imaging element. The support element stabilizes the imaging element, while the imaging element visualizes tissue in the interior body region. The support structure also carries a diagnostic or therapeutic component to contact surrounding tissue.

U.S. Pat. No. 5,876,345 to Eaton et al., which is incorporated herein by reference, describes an ultrasonic catheter for two dimensional imaging or three-dimensional reconstruction. An ultrasonic catheter including at least two ultrasonic arrays having good near and far field resolution provides an outline of a heart chamber, in order to assist in interpreting images obtained by the catheter.

U.S. Pat. No. 6,228,032 to Eaton et al., which is incorporated herein by reference, describes a steering mechanism and steering line for a catheter-mounted phased linear array of ultrasonic transducer elements.

U.S. Pat. No. 6,226,546 to Evans, which is incorporated herein by reference, describes a catheter location system for generating a three dimensional map of a part of a human body, from which three dimensional map a position of the catheter may be determined. A plurality of acoustic transducers are disposed about the catheter head at predetermined locations. A signal processing unit generates the three dimensional map responsive to signals received by a plurality of acoustic transducers acting as acoustic receivers, which acoustic signals were generated by at least one of said plurality of acoustic transducers acting as an acoustic source.

U.S. Pat. No. 6,226,542 to Reisfeld, which is assigned to the assignee of the present patent application and incorporated herein by reference, describes a method for three-dimensional reconstruction of intrabody organs. A processor reconstructs a 3D map of a volume or cavity in a patient's body from a plurality of sampled points on the volume whose position coordinates have been determined. Reconstruction of a surface is based on a limited number of sampled points. The number of sampled points is generally less than 200 points and may be less than 50 points. Preferably, ten to twenty sampled points are sufficient in order to perform a preliminary reconstruction of the surface to a satisfactory quality.

U.S. Pat. No. 6,171,248 to Hossack et al., which is incorporated herein by reference, describes an ultrasonic probe for two-dimensional imaging or three-dimensional reconstruction. The patent describes an ultrasonic probe that includes at least two ultrasonic arrays, and allows three dimensional images to be constructed of the region examined by the probe.

PCT Patent Publication WO 96/05768 to Ben-Haim et al., which is incorporated herein by reference, describes a system for determining the location and orientation of an invasive medical instrument such as a catheter or endoscope. A plurality of field generators typically outside a patient's body generate known, distinguishable fields, preferably continuous AC magnetic fields, in response to drive signals. A plurality of sensors situated in the invasive medical instrument proximate the distal end thereof generate sensor signals in response to the fields. A signal processor receiving the sensor and drive signals processes the information to determine three location coordinates and three orientation coordinates (i.e., 6 dimensions of information) relating to a point on the medical instrument.

U.S. Pat. No. 5,391,199 to Ben-Haim, which is incorporated herein by reference, describes a method for the treatment of cardiac arrhythmias, particularly, a method for ablating a portion of an organ or bodily structure of a patient. The method includes obtaining a perspective image of an organ or structure to be mapped and advancing one or more catheters having distal tips to sites adjacent to or within the organ or structure, at least one of the catheters having ablation ability. The location of each catheter's distal tip is sensed using a non-ionizing field. At the distal tip of one or more catheters, local information of the organ or structure is sensed, and the sensed information is processed to create one or more data points. The one or more data points are superimposed on a perspective image of the organ or structure, to facilitate the ablating of a portion of the organ or structure.

SUMMARY OF THE INVENTION

It is an object of some aspects of the present invention to provide improved methods and apparatus for three-dimensional mapping and geometrical reconstruction of body cavities, and particularly of chambers of the heart.

In preferred embodiments of the present invention, a cardiac catheter comprises a primary acoustic transducer and a plurality of secondary acoustic transducers distributed longitudinally along a distal portion of the catheter. The primary acoustic transducer is actuated to emit acoustic waves, preferably ultrasonic waves, while the catheter is inside a chamber of the heart. The acoustic waves are reflected from the endocardial surface of the cavity, and are received by the secondary acoustic transducers and also, typically, the primary acoustic transducer. Processing circuitry, coupled to the transducers, determines the times of flight of the received acoustic waves, thus providing a measurement of the distance from each of the transducers to a point or area on the endocardial surface. Subsequently, the primary acoustic transducer is actuated to emit acoustic waves towards other sites on the endocardium, to enable determinations of the distances from these sites to the various transducers. The distance measurements are then combined to reconstruct the three-dimensional shape of the surface, which is preferably displayed in the form of a geometrical map.

In order to direct the ultrasound from the primary acoustic transducer to the various sites on the endocardium, the catheter is preferably physically moved by the user within the chamber of the heart. Alternatively or additionally, a phased array ultrasound transducer incorporated into the primary acoustic transducer directs the ultrasound pulses to a range of sites on the endocardium. Reflected pulses from these sites are detected by the secondary acoustic transducers to enable the time of flight calculations used in the generation of the geometrical map.

For some applications, the secondary acoustic transducers are actuated individually, in sequence, to emit acoustic waves, preferably ultrasonic waves, while the catheter is inside the heart chamber.

In accordance with a preferred embodiment of the present invention, a significant portion of the endocardial surface may be mapped rapidly, typically within a single heart beat. This rapid mapping can be achieved because the acoustic waves are used to measure three-dimensional distances directly, rather than by attempting to image the heart and then extract geometrical information from the images as in methods known in the art. The distance measurements are facilitated by the unique design of the catheter, wherein the secondary acoustic transducers are distributed longitudinally along the catheter, instead of being concentrated in a phased array or other imaging configuration. In this manner, a greater range of times of flight are attained, allowing a highly-accurate assessment of the locations of the various sites on the endocardium with respect to the catheter or with respect to an absolute reference system. Preferred embodiments of the present invention also avoid the need for physical contact between the catheter and the endocardial surface during measurement.

In some preferred embodiments of the present invention, the catheter comprises one or more position sensors, which are used to determine position and orientation coordinates of the catheter within the heart. For some applications, each position sensor is associated with a particular one or set of the secondary acoustic transducers. Alternatively, one or several position sensors are placed at discrete locations on the catheter. Using the position sensors in conjunction with the acoustic measurements allows the reconstructed three-dimensional shape of the surface to be located and oriented in space. It also enables multiple measurements to be taken at different positions within the heart, during movement of the catheter, in order to enhance the accuracy of the reconstruction.

Preferably, the position sensors comprise one or more miniature coils, which are used to determine position and orientation coordinates by transmitting or receiving electromagnetic waves, as described, for example, in the above-cited PCT Patent Publication WO 96/05768 or U.S. Pat. No. 5,391,199, which are incorporated herein by reference. Alternatively, the acoustic transducers on the catheter also serve as position sensors, by receiving acoustic waves transmitted from a plurality of acoustic transducers at fixed positions outside the body, or by transmitting acoustic waves to these external transducers. The times of flight of these waves are used to determine the position and orientation of the catheter. Further alternatively, other types of position sensing systems, as are known in the art, may be used.

In further preferred embodiments of the present invention, the catheter comprises a plurality of electrodes in addition to the acoustic transducers, and is used for electrical, as well as geometrical, mapping of the heart. Preferably, the electrical mapping is performed rapidly using an array of non-contact electrodes, most preferably as described in U.S. patent application Ser. No. 09/598,862 entitled "Rapid Mapping of Electrical Activity in the Heart," filed Jun. 21, 2000 (applicant's docket no. BIO 97 US), which is assigned to the assignee of the present patent application and is incorporated herein by reference. The electrical and geometrical maps are registered to provide an integrated view of mechanical and electrical properties of the heart.

In some preferred embodiments of the present invention, other features of the acoustic waves received by the transducers on the catheter are analyzed to provide further geometrical and diagnostic information. For example, in one such embodiment, the processing circuitry analyzes the reflected waves to find reflections from both the endocardial and the epicardial surfaces. In this manner, both of the surfaces can be reconstructed simultaneously, and the thickness of the heart wall can be mapped.

In another embodiment, the processing circuitry analyzes the frequency, as well as the time of flight, of the reflected waves in order to detect a Doppler shift. The Doppler measurement is used to determine and map the heart wall velocity. This method thus enables the relative speeds of opposing or mutually-perpendicular segments of the heart wall to be measured simultaneously. By contrast, methods of echo Doppler measurement known in the art use a probe outside the body and therefore can measure wall velocity of only one side of the heart at any given time.

Although preferred embodiments are described herein with reference to cardiac catheters for mapping chambers of the heart, other applications of the present invention will be apparent to those skilled in the art. These applications include, but are not limited to, mapping and geometrical reconstruction of other body cavities, such as the coronary arteries or the gastrointestinal system.

There is therefore provided, in accordance with a preferred embodiment of the present invention, apparatus for mapping a surface of a cavity within a body of a subject, including:

an elongate probe, having a longitudinal axis and including a distal portion adapted for insertion into the cavity;

a primary acoustic transducer on the distal portion of the probe, adapted to emit acoustic waves while the probe is in the cavity; and a plurality of secondary acoustic transducers, distributed along the longitudinal axis over the distal portion of the probe, which are adapted to receive the acoustic waves after reflection of the waves from the surface of the cavity and to generate, responsive to the received waves, electrical signals indicative of times of flight of the waves.

Preferably, the apparatus includes apparatus for mapping a chamber of the heart of the subject, and the probe includes an intracardiac catheter.

In a preferred embodiment, the primary acoustic transducer includes a phased array ultrasound transducer. Alternatively, the primary acoustic transducer includes an ultrasound transducer configured only for non-phased array operation. Further alternatively or additionally, the secondary acoustic transducers include ultrasound transducers configured only for non-phased array operation.

Preferably, the probe includes at least one position sensor, which is adapted to generate a position signal indicative of position coordinates of the probe within the body. Preferably, the apparatus further includes control circuitry, adapted to process the electrical signals generated by the secondary acoustic transducers responsive to the position signal, so as to reconstruct a three-dimensional shape of the surface of the cavity based on the times of flight and the position signal. Typically, the position sensor includes a coil, and the position signal includes an electrical current induced in the coil by an externally-applied magnetic field.

Additionally or alternatively, the at least one position sensor includes a plurality of position sensors. Preferably, one of the plurality of position sensors is disposed on the probe near a first subset of the secondary acoustic transducers, and another one of the plurality of position sensors is disposed on the probe near a second subset of the secondary acoustic transducers, and the apparatus includes control circuitry, adapted to process the electrical signals generated by the secondary acoustic transducers responsive to position signals generated by the first and second position sensors, so as to reconstruct a three-dimensional shape of the surface of the cavity based on the times of flight and the position signals.

Preferably, the apparatus includes control circuitry, adapted to receive and to process the electrical signals generated by the secondary acoustic transducers so as to reconstruct a three-dimensional shape of the surface of the cavity based on the times of flight. Most preferably, responsive to the times of flight, the circuitry is adapted to determine distances from the secondary acoustic transducers to respective points on the surface of the cavity, and to combine the determined distances so as to reconstruct the shape. Additionally or alternatively, the circuitry is operative to distinguish the signals generated responsive to the waves that have undergone one reflection from the surface of the cavity from the signals generated responsive to the waves that have undergone multiple reflections, and to reject the signals due to the waves that have undergone the multiple reflections. Further additionally or alternatively, the circuitry is adapted to detect a spectral shift in the acoustic waves received by the secondary acoustic transducers and to determine, responsive to the spectral shift, a velocity of motion of the surface.

Typically, the apparatus includes a display, which is driven by the circuitry to display an image of the three-dimensional shape.

In a preferred embodiment, the primary acoustic transducer is adapted to emit a plurality of bursts of acoustic waves from a respective plurality of dispositions within the cavity, wherein the secondary acoustic transducers are adapted to receive the bursts of acoustic waves after reflection of the bursts from the surface of the cavity, and to generate, responsive to the received bursts, electrical signals indicative of times of flights of the bursts, and wherein the circuitry is adapted to reconstruct the three-dimensional shape of the surface based on the times of flight of the bursts. Preferably, the primary acoustic transducer is adapted to be moved through the plurality of dispositions by a user of the apparatus.

Typically, the cavity has a wall, and the surface includes an inner surface of the wall and an outer surface of the wall, and the circuitry is adapted to distinguish the signals generated responsive to the waves that have been reflected from the inner surface from the signals generated responsive to the waves that have been reflected from the outer surface. Preferably, the circuitry is operative to determine a thickness of the wall responsive to the signals generated by the waves that have been reflected from the inner surface and the waves that have been reflected from the outer surface.

In a preferred embodiment, the apparatus includes one or more electrodes disposed on the distal portion of the probe, which are adapted to convey electrical signals to the circuitry responsive to electrical activity in the cavity, wherein the circuitry is adapted, responsive to the signals from the electrodes, to superimpose an indication of the electrical activity on the three-dimensional shape of the surface. Preferably, the indication of the electrical activity includes a map of electrical potentials at the surface of the cavity, which is registered with the three-dimensional shape of the surface.

In another preferred embodiment, the apparatus includes a plurality of reference transducers outside the body, which are adapted to transmit acoustic waves into the body, such that the waves are received by the secondary acoustic transducers on the probe, causing the secondary acoustic transducers to generate electrical reference signals, wherein the circuitry is adapted to process the reference signals so as to determine position coordinates of the probe. Preferably, responsive to the determined position coordinates, the circuitry is adapted to define a position of the three-dimensional shape within the body.

In a preferred embodiment, the apparatus includes one or more electrodes disposed on the distal portion of the probe, which are adapted to detect electrical activity in the cavity. Preferably, the one or more electrodes are adapted to detect varying electrical potentials at the surface of the cavity, wherein the one or more electrodes include an array of non-contact electrodes, which are adapted to detect the varying electrical potentials at the surface, substantially without making contact with the surface.

There is also provided, in accordance with a preferred embodiment of the present invention, a method for mapping a surface of a cavity within a body of a subject, including:
inserting a probe into the cavity, the probe having a longitudinal axis;
emitting acoustic waves within the cavity from a primary point on the probe;
receiving the acoustic waves at each of a plurality of secondary points distributed along the longitudinal axis of the probe, following reflection of the emitted waves from the surface of the cavity;
analyzing the received waves to determine times of flight of the waves; and
reconstructing a three-dimensional shape of the surface of the cavity based on the determined times of flight.

Preferably, emitting and receiving the waves include emitting and receiving the waves while the probe is held substantially stationary at a single location in the cavity, and reconstructing the three-dimensional shape includes reconstructing the shape based substantially only on the waves received at the single location.

Preferably, the method includes determining position coordinates of the probe inside the body, wherein reconstructing the three-dimensional shape includes reconstructing the shape responsive to the coordinates. Further preferably, reconstructing the shape includes defining a position of the shape inside the body using the coordinates. Most preferably, emitting and receiving the waves include emitting and receiving the waves at a plurality of different locations of the probe in the cavity, and reconstructing the shape includes reconstructing the shape based on the waves received at the different locations, using the coordinates of the probe determined at the different locations.

Additionally or alternatively, determining the position coordinates includes transmitting and receiving reference acoustic waves between reference points outside the body and the points on the probe, and analyzing the received reference waves to find distances between the reference points and the points on the probe, thus to determine the position coordinates.

Preferably, reconstructing the shape includes determining, responsive to the times of flight, distances from the secondary points to corresponding points on the surface of the cavity generally opposite the secondary points, and combining the determined distances so as to reconstruct the shape. Most preferably, determining the distances includes distinguishing the waves received at the secondary points after one reflection from the surface of the cavity from the waves received after multiple reflections, and rejecting the waves received after the multiple reflections.

Typically, the cavity has a wall, and the surface includes an inner surface of the wall and an outer surface of the wall, and determining the distances includes distinguishing the waves received at the secondary points after reflection from the inner surface from the waves received after reflection from the outer surface. Preferably, reconstructing the shape includes determining a thickness of the wall by comparing the times of flight of the waves received after reflection from the inner surface to those of the waves received after reflection from the outer surface.

In a preferred embodiment, the method includes analyzing the received waves to detect a spectral shift therein, so as to determine, responsive to the spectral shift, a velocity of motion of the surface. Preferably, reconstructing the shape includes generating a map of the cavity that includes an indication of the velocity of motion of different areas of the surface.

In another preferred embodiment, the method includes sensing electrical activity in the cavity using electrical sensors on the probe. Preferably, sensing the electrical activity includes detecting varying electrical potentials at the surface of the cavity substantially without contact between the electrical sensors on the probe and the surface. Additionally or alternatively, reconstructing the shape includes superimposing an indication of the electrical activity on the reconstructed three-dimensional shape of the surface. Preferably, superimposing the indication of the electrical activity includes generating a map of electrical potentials at the surface of the cavity, and registering the map with the three-dimensional shape of the surface.

The present invention will be more fully understood from the following detailed description of the preferred embodiments thereof, taken together with the drawings, in which:

DETAILED DESCRIPTION OF PREFERRED EMBODIMENTS

Figure 1:
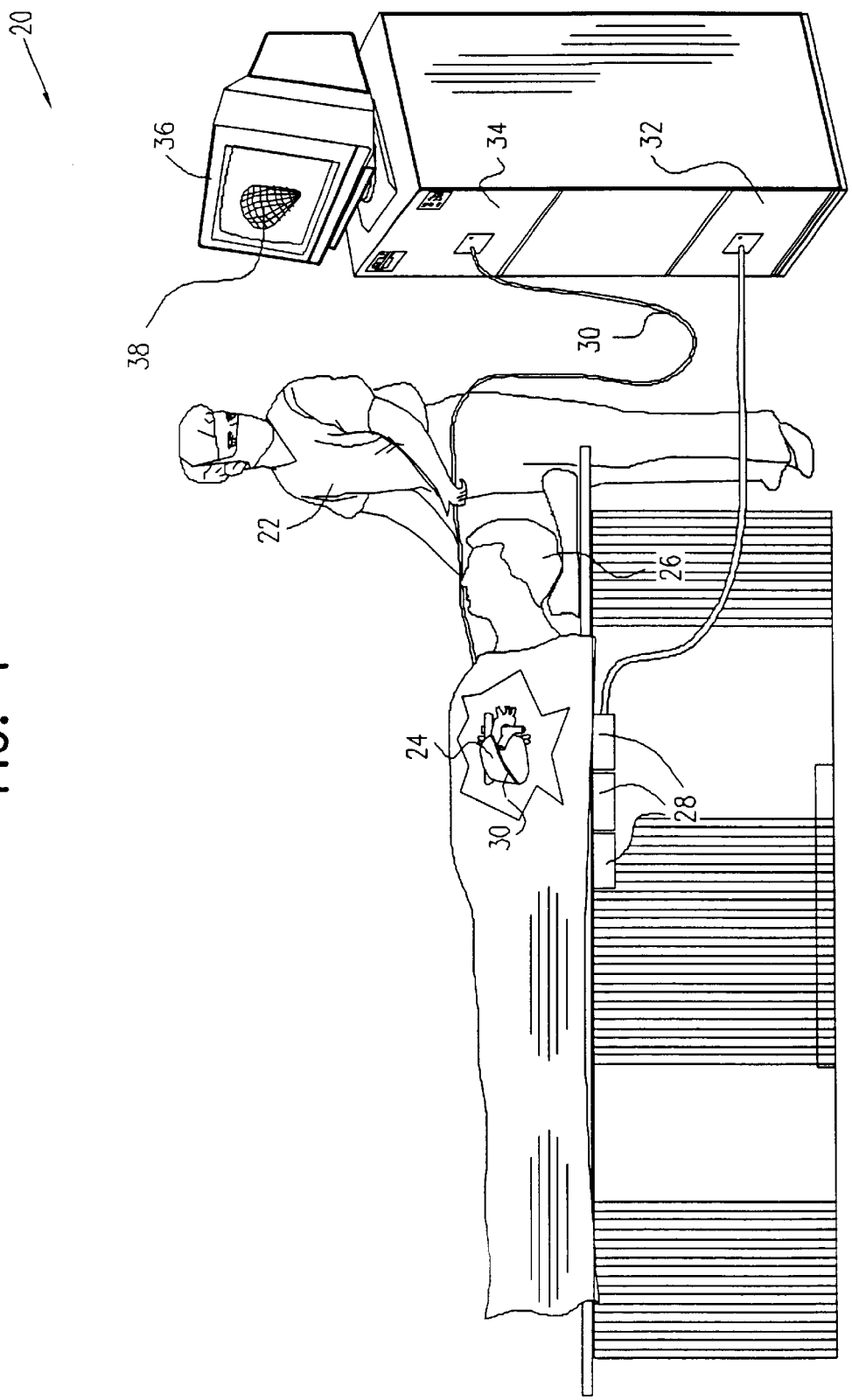
FIG. 1 is a schematic, pictorial illustration of a system for geometrical mapping of the heart, in accordance with a preferred embodiment of the present invention.

FIG. 1 is a schematic, pictorial illustration of a mapping system 20, for three-dimensional geometrical mapping of a heart 24 of a subject 26, in accordance with a preferred embodiment of the present invention. System 20 comprises an elongate probe, preferably a catheter 30, which is inserted by a user 22 through a vein or artery of the subject into a chamber of the heart.

Figure 2:
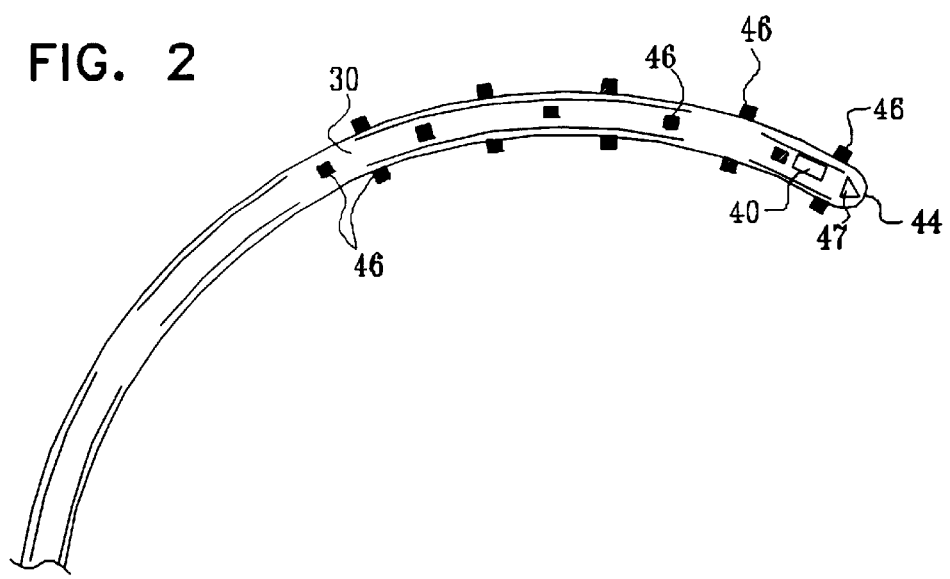
FIG. 2 is a schematic, pictorial illustration of a distal portion of a catheter for use in the system of FIG. 1, in accordance with a preferred embodiment of the present invention.

FIG. 2 is a schematic, pictorial illustration showing a distal portion of catheter 30, which is inserted into heart 24. The catheter has a primary ultrasound transducer 47 and an array of secondary ultrasonic transducers 46 on its outer surface, preferably five to twenty such transducers, each about 0.5 mm in size, arrayed longitudinally along the catheter proximal to a distal end 44 thereof. Typically, the secondary ultrasound transducers 46 are mutually spaced along catheter 30 by up to several centimeters. Optionally, the catheter may also comprise electrodes, as described below, and other diagnostic and therapeutic features (not shown in the figures), as are known in the art.

Catheter 30 preferably comprises at least one position sensor 40, most preferably located near distal tip 44. Preferably, a plurality of position sensors 40 are deployed in the catheter, preferably near a proximal end of the array of transducers. Alternatively, each position sensor 40 is in a vicinity of a single one of the secondary ultrasound transducers or in a vicinity of a set of the secondary ultrasound transducers. Sensor 40 preferably comprises an electromagnetic sensor, which is mounted within the catheter by any suitable method, for example, using polyurethane glue or the like. The sensor is electrically connected to an electromagnetic sensor cable (not shown), which extends through the catheter body and into a control handle of the catheter. The electromagnetic sensor cable comprises multiple wires encased within a plastic covered sheath. Within the catheter body, the sensor cable may be enclosed within a protective sheath along with lead wires of the ultrasound transducers, if desired. In the control handle, the wires of the sensor cable are connected to a circuit board (not shown), which amplifies the signals received from the electromagnetic sensor and transmits them to a computer housed in a console 34 (FIG. 1), in a form understandable to the computer. Also, because the catheter is designed for single use only, the circuit board preferably contains an EPROM chip, which shuts down the circuit board after the catheter has been used. This prevents the catheter, or at least the electromagnetic sensor, from being used twice.

A suitable electromagnetic sensor is described, for example, in U.S. Pat. No. 5,391,199, which is incorporated herein by reference. A preferred electromagnetic mapping sensor is manufactured by Biosense, Ltd. (Tirat Hacarmel, Israel), and marketed under the trade designation NOGA.

To use the electromagnetic sensor, the patient is placed in a magnetic field generated, for example, by placing under the patient a pad containing field generator coils 28 (FIG. 1) for generating a magnetic field. A reference electromagnetic sensor (not shown) is preferably fixed relative to the patient, e.g., taped to the patient's back, and catheter 30 containing sensor 40 is advanced into the patient's heart 24. Sensor 40 typically comprises three small coils (preferably mutually-orthogonal coils) which in the magnetic field generate weak electrical signals indicative of their position in the magnetic field. Signals generated by both the fixed reference sensor and by sensor 40 in the heart are amplified and transmitted to console 34, which analyzes the signals and then displays the signals on a monitor 36. By this method, the precise location of sensor 40 in the catheter relative to the reference sensor can be ascertained and visually displayed. The sensors can also detect displacement of the catheter that is caused by contraction of the heart muscle.

Some of the features of catheter 30 and system 20 are implemented in the NOGA-STAR catheter marketed by Biosense Webster, Inc., and in the above-mentioned Biosense-NOGA system, also marketed by Biosense Webster, Inc. Further aspects of the design of catheter 30 and of system 20 generally are described in U.S. patent application Ser. No. 09/506,766, which is assigned to the assignee of the present patent application and is incorporated herein by reference. The detailed design of catheter 30 and the geometrical and electrical mapping functions carried out using the catheter and system 20, however, as described hereinbelow, are unique to the present invention.

As noted above, sensor 40 preferably comprises three non-concentric coils, such as those described in the above-mentioned PCT Patent Publication WO 96/05768. The coils sense magnetic fields generated by field generator coils 28, which are driven by driver circuits 32 (FIG. 1).

Alternatively, the sensors may generate fields, which are detected by coils 28. System 20 thus achieves continuous generation of six dimensions of position and orientation information relating to sensor 40. Alternatively, sensor 40 (and, optionally, additional position sensors in catheter 30) may comprise a single coil, which is sufficient, in conjunction with field generator coils 28, to generate three dimensions of position and two dimensions of orientation information. The third dimension of orientation (typically rotation of catheter 30 about its longitudinal axis) can be inferred if needed from a comparison of the coordinates of two such sensors provided at mutually-spaced locations in the catheter and/or from mechanical information pertaining to the catheter itself, e.g., bending moments of the catheter.

Further alternatively, the sensors may comprise other types of position and/or coordinate sensors, as described, for example, in U.S. Pat. Nos. 5,391,199 or 5,443,489 or in PCT publication WO 94/04938, each of which is incorporated herein by reference, or substantially any other suitable type of position/coordinate sensing device known in the art. Still further alternatively or additionally, catheter 30 is marked with one or more markers whose positions can be determined from outside of the body, such as radio-opaque markers for use with a fluoroscope.

As noted above, catheter 30 is coupled to console 34, which enables the user to observe and regulate the functions of the catheter. Console 34 includes a processor, preferably a computer with appropriate signal processing circuits (which are typically contained inside a housing of the computer). The processor is coupled to drive monitor 36. The signal processing circuits typically generate drive signals, causing primary ultrasound transducer 47 to emit an ultrasonic pulse. The circuits further receive, amplify, filter and digitize signals from catheter 30, including signals generated by position sensor 40 secondary ultrasound transducers 46, and, optionally, primary ultrasound transducer 47. The digitized signals are received and used by the console to compute the position and orientation of the catheter and to extract the times of flight of the acoustic waves within the heart. The information derived from this analysis is used to reconstruct a three-dimensional geometrical map 38 of the endocardial surface of heart 24.

Typically, system 20 includes other elements, which are not shown in the figures for the sake of simplicity. Some of these elements are described, for example, in U.S. patent application Ser. No. 09/122,137, which is assigned to the assignee of the present patent application, and whose disclosure is incorporated herein by reference. For instance, system 20 may include an ECG monitor, coupled to receive signals from one or more body surface electrodes, so as to provide an ECG synchronization signal to console 34. As mentioned above, the system typically also includes a reference position sensor, either on an externally-applied reference patch attached to the exterior of the patient's body, or on an internally-placed catheter, which is inserted into heart 24 and maintained in a fixed position relative to the heart. By comparing the position of catheter 30 to that of the reference catheter, the coordinates of catheter 30 are accurately determined relative to the heart, irrespective of heart motion. Alternatively, any other suitable method may be used to compensate for heart motion.

Figure 3:
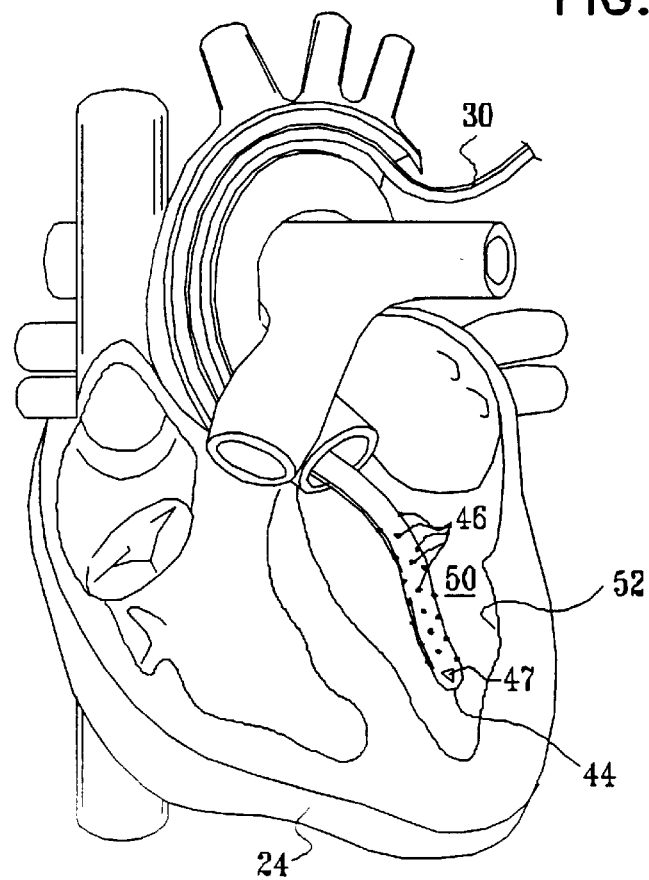
FIG. 3 is a schematic, cutaway illustration of a heart into which the catheter of FIG. 2 has been inserted, in accordance with a preferred embodiment of the present invention.

FIG. 3 is a schematic, sectional illustration of heart 24, showing the distal portion of catheter 30 inserted through the aorta into a left ventricle 50 of the heart, in accordance with a preferred embodiment of the present invention. Primary ultrasound transducer 47 is driven by console 34 to emit ultrasonic waves toward endocardium 52. Secondary ultrasound transducers 46 receive the waves reflected back from the heart wall and generate electrical signals, which are conveyed to console 34 for processing and analysis. There is no need for tip 44 or for any other portion of catheter 30 to contact the endocardium during the ultrasonic measurements.

Figure 4:
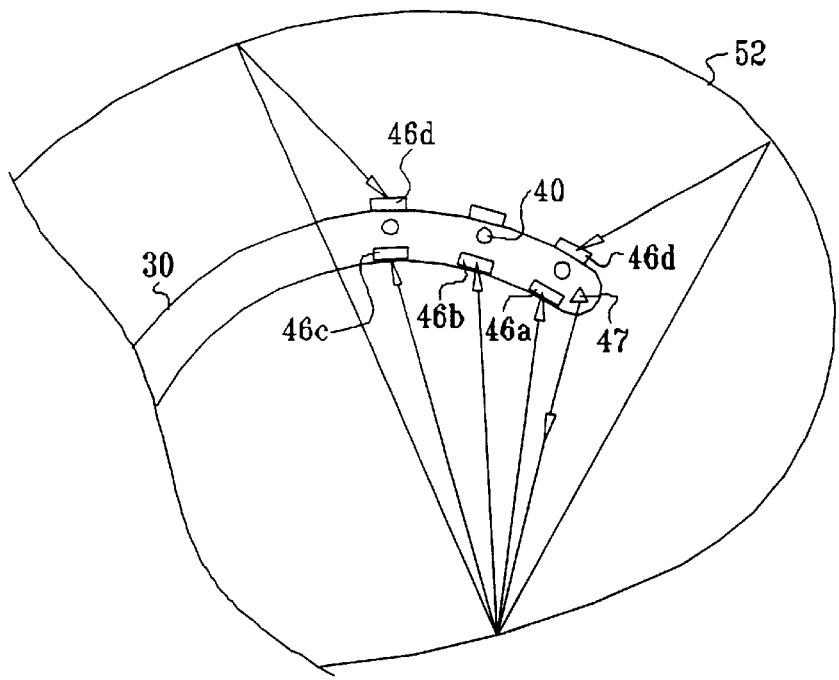
FIG. 4 is a schematic detail of the heart and catheter of FIG. 3, illustrating reflections of acoustic waves from an inner surface of a heart chamber, in accordance with a preferred embodiment of the present invention.
Figure 5:
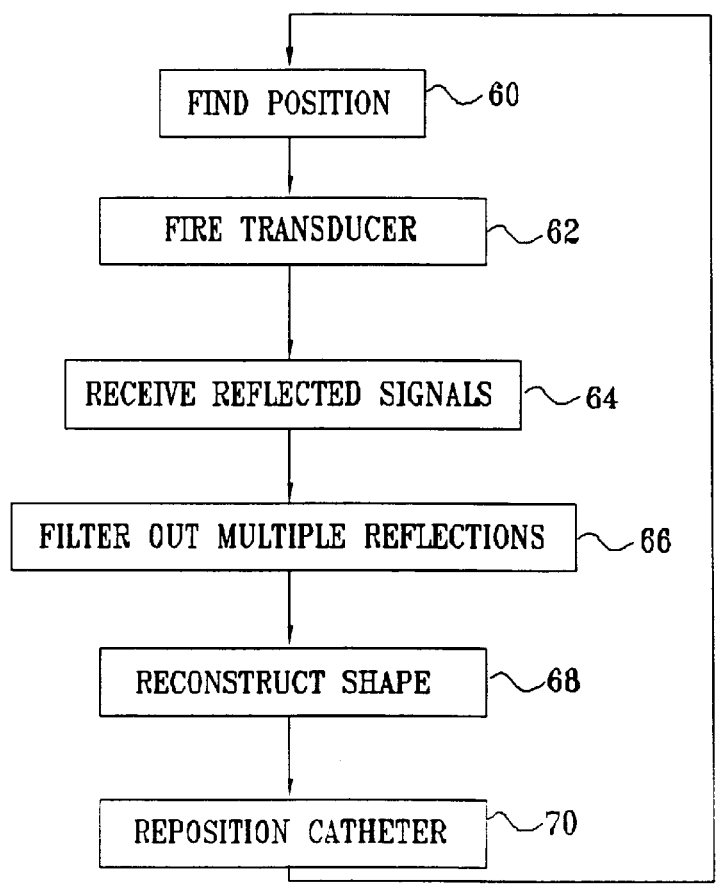
FIG. 5 is a flow chart that schematically illustrates a method for generating a three-dimensional reconstruction of the inner surface of the heart, in accordance with a preferred embodiment of the present invention.

Reference is now made to FIGS. 4 and 5, which schematically illustrate a method for three-dimensional geometrical mapping and reconstruction of ventricle 50, in accordance with a preferred embodiment of the present invention. FIG. 4 shows a detail of catheter 30 inside the ventricle, in which a number of transducers 46 are labeled 46a, 46b, 46c, and 46d, for the purpose of the description below. (For simplicity, the remainder of secondary ultrasound transducers 46 are not shown in this figure.) FIG. 5 is a flow chart that details the steps in the method. Although this method is described with reference to mapping of left ventricle 50, it will be appreciated that it is similarly applicable to mapping other chambers of heart 24, as well as to mapping of other body cavities.

At a positioning step 60, catheter 30 is inserted into ventricle 50, or moved therein, and is positioned in a desired location and orientation by user 22. Preferably, more than one position sensor 40 is used to determine position and orientation coordinates of the secondary ultrasound transducers and/or of the distal portion of the catheter inside the heart, as described above. Alternatively, however, position sensing may be omitted, and endocardium 52 may be geometrically reconstructed without a specific absolute position reference. Such position-independent reconstruction is possible as long as all of the necessary signals are collected from transducers 46 within a period short enough so that the heart can be considered to be stationary during the measurement, i.e., in a space of time considerably shorter than a single heart beat. Such rapid measurement is feasible using system 20, as described in greater detail hereinbelow.

At a transducer firing step 62, primary ultrasound transducer 47 on catheter 30 is actuated by a signal from console 34. The actuation causes the transducer to emit an ultrasonic pulse, preferably at a frequency of about 5–9 MHz and with a duration of about 1 microsecond. The emitted ultrasonic waves preferably form a beam having a narrow divergence angle, preferably less than 20°, and most preferably about 3°. The beam impinges on an area that is typically about 4 mm in diameter on endocardium 52, at a site on endocardium 52 that is determined by the disposition of catheter 30 within ventricle 50. The size of the beam on the endocardium is determined by the distance of the transducer from the endocardium, which will typically be about 2–3 cm, depending on the dimensions of the heart.

The waves emitted by transducer 47 bounce off the inner surface of endocardium 52 and are reflected back first to transducers 46a, 46b, and 46c, which are typically closest to the target site on endocardium 52, and, subsequently, to transducers 46d and other secondary ultrasound transducers 46 on catheter 30. Assuming the reflection to include both diffuse and specular components, the reflected energy will largely be concentrated on only some of transducers 46. These waves are received by transducers 46 at a reflection reception step 64, generating electrical signals that are processed by console 34. The console finds the time of flight of the waves received at each of the transducers by comparing the arrival time of the electrical signals to the actuation time of primary ultrasound transducer 47. This time of flight is proportional to the length of the path traversed from transducer 47 to endocardium 52 and back to transducers 46. The path length thus determined from the time of flight information is used in reconstructing the geometrical shape of ventricle 50, as described below. Based on the size of the typical heart, the time of flight is generally less than 50 microseconds.

The ultrasonic waves emitted by primary ultrasound transducer 47 are most strongly reflected from endocardium 52, i.e., from the inner surface of ventricle 50. There may also be reflections, however, from the epicardium of the ventricle and from other structures in proximity to the ventricle. Therefore, to determine the time of flight at step 64, console 34 preferably measures for each transducer 46 the arrival time of the first strong peak in the signals generated by the transducer upon receiving the reflected waves. This peak corresponds to reflection from endocardium 52. Optionally, the console may also detect and measure the arrival time of a second peak in each signal, which typically corresponds to reflection from the epicardium. The difference between the arrival times of the first and second peaks gives a measure of the local thickness of the heart wall.

As a further option, console 34 determines not only the arrival times of the reflected waves at transducers 46, but also finds frequency spectra of the waves, as is known in the art. If the heart wall is moving toward or away from any one of secondary ultrasound transducers 46 at the time a wave strikes the endocardium, the reflected waves will undergo a Doppler shift. The frequency spectra will therefore indicate the velocity of the heart wall relative to the catheter. Console 34 preferably analyzes this spectral information, in conjunction with the distance information provided by the time of flight, in order to measure the wall velocity.

Multiple reflections within ventricle 50 may also occur, as illustrated, for example, by the two-bounce path from primary ultrasound transducer 47 to secondary ultrasound transducers 46d, shown in FIG. 4. The path length measured in this case for the waves received at these transducers will therefore provide confusing geometrical information regarding ventricle 50, and should be ignored. To avoid being confused by multiple-bounce signals, console 34 rejects the signal received from transducer 46d, at a multiple-reflection filtering step 66. Such signals are preferably detected by setting a maximum time of flight from primary ultrasound transducer 47 to any other transducer, and discarding measurements in excess of this maximum. Alternatively or additionally, only ultrasound pulses received at a small number of secondary ultrasound transducers 46 are processed. For example, the first three or the first six transducers 46 to receive ultrasound pulses have their data analyzed, and the remaining data are not processed.

In a preferred embodiment, primary ultrasound transducer 47 comprises a phased array ultrasound transducer, and step 62 comprises emitting pulses from transducer 47 to a range of sites within endocardium 52. In this manner, it is possible to measure distances from each of secondary ultrasound transducers 46 to a large number of points distributed over all or a substantial portion of endocardium 52, preferably within a time considerably less than a single heart beat. The secondary ultrasound transducers, however, preferably do not comprise phased array ultrasound transducers.

At a shape reconstruction step 68, console 34 combines the distance data deduced from the measured times of flight to incrementally build a three-dimensional geometrical map of ventricle 52. For embodiments in which primary ultrasound transducer 47 does not include a phased array ultrasound transducer, random or planned motion of catheter 30 (e.g., in a catheter reposition step 70) typically causes the pulses emitted by primary ultrasound transducer 47 to reflect off of a representative subset of points on the endocardial wall, sufficient to enable a reconstruction of the shape of ventricle 50. In this case (as well as optionally in the case of the phased array ultrasound transducer), one or more position sensors 40 are preferably used, as shown, to facilitate a determination of absolute coordinates of the various points of the endocardial surface.

Preferably, points from the various measurements are placed in a three-dimensional space, and a surface is fitted to the points in order to generate map 38. Further preferably, the reconstruction is carried out using methods described in European patent application EP 0 974 936 or the above-mentioned U.S. patent application Ser. No. 09/122,137. Alternatively, other methods of geometrical reconstruction may be used, as are known in the art.

For embodiments in which primary ultrasound transducer 47 comprises a phased array ultrasound transducer, a generally-complete reconstruction of endocardium 52 of ventricle 50 is typically generated irrespective of motion of catheter 30, and, consequently, no position sensor 40 needs to be incorporated into catheter 30. In this case, the coordinates of the points on the endocardium are found in a frame of reference determined arbitrarily by the (unknown) position of the catheter. However, regardless of whether a phased array ultrasound transducer is used, if the positions of the secondary ultrasound transducers 46 are determined using a position sensor 40, then the accuracy of the reconstruction can be increased by repositioning catheter 30 at repositioning step 70, and repeating steps 60 through 68. Preferably, the additional points on the endocardial surface that are found at this step are used to refine and correct map 38 that was generated in the preceding iteration. Measurements at multiple different positions of the catheter may be carried out and combined in this manner.

To the extent that console 34 gathered other information in conjunction with finding the times of flight, this information is preferably shown in map 38, as well. For example, the map may show both endocardial and epicardial surfaces, preferably with the option of showing a sectional view in a desired plane through the heart to allow the wall thickness to be visualized. If Doppler measurements are made, the map preferably shows the wall velocity as a function of position, by color coding, for example. The velocity information may be used to calculate a measure of the heart's contraction strength or efficiency. The geometrical map may also display electrical information, as described below.

Figure 6:
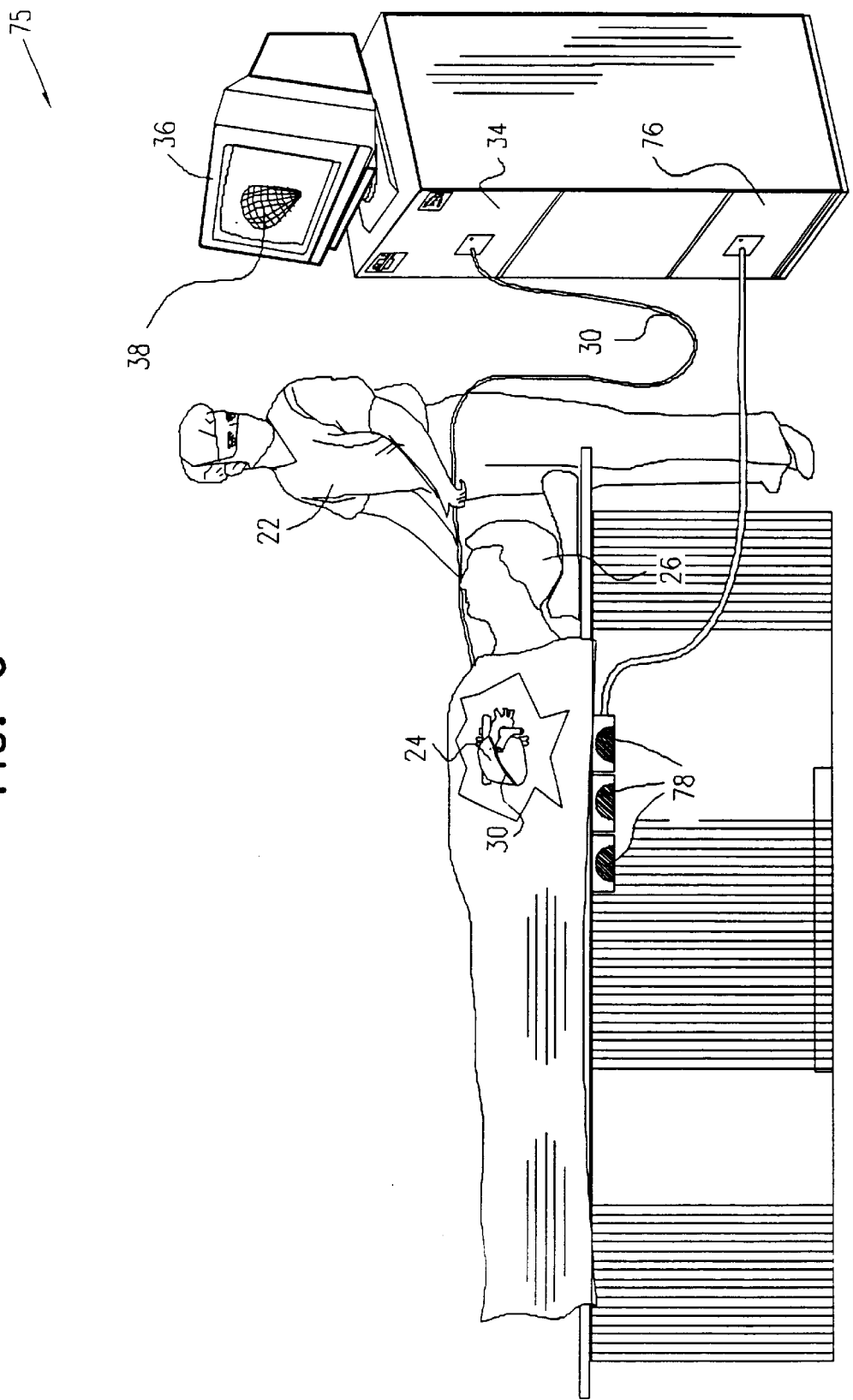
FIG. 6 is a schematic, pictorial illustration of a system for geometrical mapping of the heart, in accordance with another preferred embodiment of the present invention.

FIG. 6 is a schematic, pictorial illustration of a system 75 for geometrical mapping of heart 24, in accordance with another preferred embodiment of the present invention. System 75 is substantially identical to system 20, shown in FIG. 1 and described hereinabove, except for its mode of determining the position of catheter 30 inside heart 24. In place of magnetic position determination using sensor 40 in catheter 30, system 75 uses transducers 46 and/or 47 on catheter 30 to determine the catheter's position ultrasonically.

For this purpose, a number of ultrasonic transmitters 78, preferably having a generally spherical or hemispherical shape, are positioned outside the body of patient 26 and irradiate the vicinity of heart 24 with ultrasonic waves. In the present embodiment, the transmitters are positioned under the patient's back. Transmitters 78 are preferably driven in sequence by an ultrasonic driver 76 to emit their ultrasonic waves. The waves are received by transducers 46 and/or 47 on catheter 30, and the times of flight of the waves are measured to determine the distances between selected points on the catheter and the known locations of the transmitters. (Alternatively, transducers 46 and/or 47 may emit signals, to be detected by fixed receivers outside the body, in place of transmitters 78.) The distances are triangulated to find position coordinates of the catheter in the heart.

Thus, in the embodiment of FIG. 6, transducers 46 and/or 47 serve as both position sensors and mapping detectors. Consequently, system 75 will generally be lower in cost than system 20. Although magnetic position sensing is typically more accurate than ultrasonic position sensing, the ultrasonic sensing mode of the present embodiment is adequate for most applications of the system, since it is typically necessary to determine only relative positions of catheter 30 and heart 24, and not absolute positions.

Figure 7:
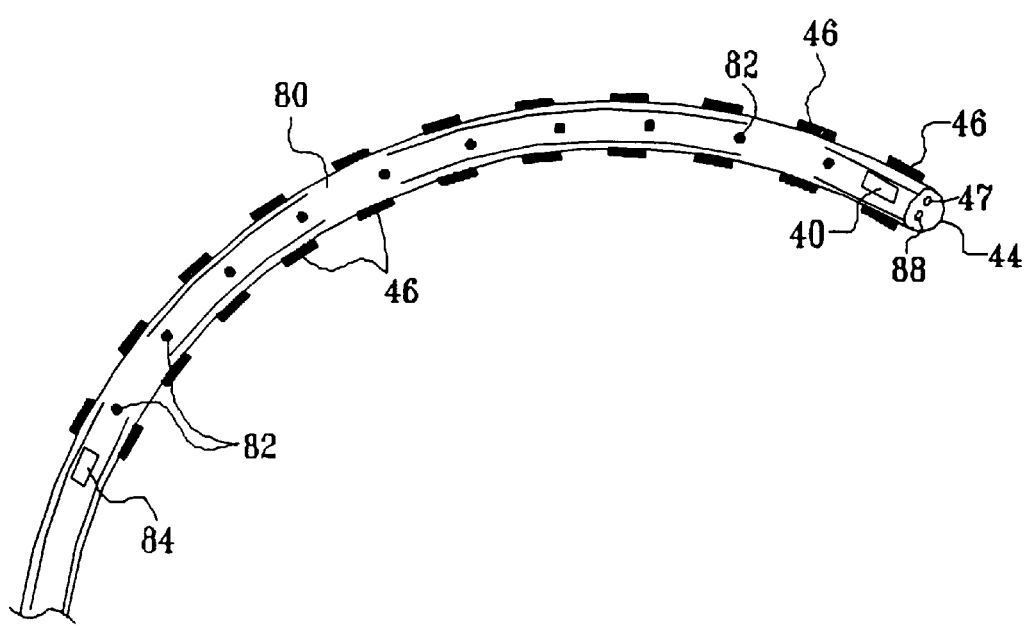
FIG. 7 is a schematic, pictorial illustration of a distal portion of a catheter for use in geometrical and electrical mapping of the heart, in accordance with a preferred embodiment of the present invention.

FIG. 7 is a schematic, pictorial illustration of a catheter 80 for use in system 20 or system 75, in accordance with still another preferred embodiment of the present invention. Catheter 80 is largely similar to catheter 30, but is also adapted to make electrophysiological measurements, in conjunction with the geometrical mapping functions described in detail hereinabove. For this purpose, catheter 80 comprises, in addition to transducers 46, an array of non-contact electrodes 82, distributed proximally to distal end 44 of the catheter. These electrodes are preferably used to perform rapid electrical mapping of endocardium 52, most preferably as described in the above-mentioned U.S. patent application entitled "Rapid Mapping of Electrical Activity in the Heart." Alternatively or additionally, catheter 80 comprises one or more contact electrodes 88. Preferably, an additional position sensor 84 is provided, so that the positions of all of electrodes 82 can be accurately determined.

In operation, console 34 receives both acoustic signals from transducers 46 and electrical signals from electrodes 82. The acoustic signals are used to reconstruct the three-dimensional geometrical shape of ventricle 50, as described above. The console uses this geometrical information, together with the electrical signals, to generate a three-dimensional map of electrical potentials at surface 52 of the ventricle. The electrical map is preferably superposed on geometrical map 38, in the form of contour lines or color coding, for example, in order to provide an integrated, electrical and mechanical picture of the ventricle.

This rapid acoustical and electrical mapping using ultrasound transducers 46 and electrodes 82 may be supplemented with contact measurements for enhanced accuracy at particular points. For example, an optional electrode 88 at the distal tip of catheter 80 may be brought into contact with points on the endocardium to measure electrical potentials at these points. Meanwhile, position sensor(s) 40 provides an accurate reading of the position coordinates of electrode 88. Additional data points gathered in this manner are preferably marked on map 38. Alternatively, electrode 88 may be driven to ablate areas of the endocardial surface in order to treat arrhythmias detected in an earlier mapping stage, for example. Other modes of therapy, as are known in the art, may also be administered by a suitably-configured catheter, in conjunction with the mapping and reconstruction functions provided by these embodiments of the present invention.

Although preferred embodiments are described herein with reference to cardiac catheters 30 and 75, for mapping chambers of heart 24, other applications of the principles of the present invention will be apparent to those skilled in the art. These applications include, but are not limited to, mapping and geometrical reconstruction of other body cavities, such as the coronary arteries or the gastrointestinal system.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for mapping a surface of a cavity within a body of a subject, comprising:

an elongate probe, having a longitudinal axis and comprising a distal portion adapted for insertion into the cavity;

a primary acoustic transducer on the distal portion of the probe, adapted to emit acoustic waves while the probe is in the cavity;

a plurality of secondary acoustic transducers, distributed along the longitudinal axis over the distal portion of the probe, which are adapted to receive the acoustic waves after reflection of the waves from the surface of the cavity and to generate, responsive to the received waves, electrical signals indicative of times of flight of the waves; and control circuitry, adapted to receive and to process the electrical signals generated by the secondary acoustic transducers so as to reconstruct a three-dimensional shape of the surface of the cavity based on the times of flight, wherein the circuitry is operative to distinguish the signals generated responsive to the waves that have undergone one reflection from the surface of the cavity from the signals generated responsive to the waves that have undergone multiple reflections, and to reject the signals due to the waves that have undergone the multiple reflections.

2. Apparatus according to claim 1, wherein the apparatus comprises apparatus for mapping a chamber of the heart of the subject, and wherein the probe comprises an intracardiac catheter.

3. Apparatus according to claim 1, wherein the primary acoustic transducer comprises a phased array ultrasound transducer.

4. Apparatus according to claim 1, wherein the primary acoustic transducer comprises an ultrasound transducer configured only for non-phased array operation.

5. Apparatus according to claim 1, wherein the secondary acoustic transducers comprise ultrasound transducers configured only for non-phased array operation.

6. Apparatus according to claim 1, wherein the probe comprises at least one position sensor, which is adapted to generate a position signal indicative of position coordinates of the probe within the body.

7. Apparatus according to claim 6, and comprising control circuitry, adapted to process the electrical signals generated by the secondary acoustic transducers responsive to the position signal, so as to reconstruct a three-dimensional shape of the surface of the cavity based on the times of flight and the position signal.

8. Apparatus according to claim 6, wherein the position sensor comprises a coil, and wherein the position signal comprises an electrical current induced in the coil by an externally-applied magnetic field.

9. Apparatus according to claim 6, wherein the at least one position sensor comprises a plurality of position sensors.

10. Apparatus according to claim 9, wherein one of the plurality of position sensors is disposed on the probe near a first subset of the secondary acoustic transducers, and wherein another one of the plurality of position sensors is disposed on the probe near a second subset of the secondary acoustic transducers, and wherein the apparatus comprises control circuitry, adapted to process the electrical signals generated by the secondary acoustic transducers responsive to position signals generated by the first and second position sensors, so as to reconstruct a three-dimensional shape of the surface of the cavity based on the times of flight and the position signals.

11. Apparatus according to claim 1, wherein responsive to the times of flight, the circuitry is adapted to determine distances from the secondary acoustic transducers to respective points on the surface of the cavity, and to combine the determined distances so as to reconstruct the shape.

12. Apparatus according to claim 1, wherein the circuitry is adapted to detect a spectral shift in the acoustic waves received by the secondary acoustic transducers and to determine, responsive to the spectral shift, a velocity of motion of the surface.

13. Apparatus according to claim 1, and comprising a display, which is driven by the circuitry to display an image of the three-dimensional shape.

14. Apparatus according to claim 1, wherein the primary acoustic transducer is adapted to emit a plurality of bursts of acoustic waves from a respective plurality of dispositions within the cavity, wherein the secondary acoustic transducers are adapted to receive the bursts of acoustic waves after reflection of the bursts from the surface of the cavity, and to generate, responsive to the received bursts, electrical signals indicative of times of flights of the bursts, and wherein the circuitry is adapted to reconstruct the three-dimensional shape of the surface based on the times of flight of the bursts.

15. Apparatus according to claim 14, wherein the primary acoustic transducer is adapted to be moved through the plurality of dispositions by a user of the apparatus.

16. Apparatus according to claim 1, wherein the cavity has a wall, and the surface comprises an inner surface of the wall and an outer surface of the wall, and wherein the circuitry is adapted to distinguish the signals generated responsive to the waves that have been reflected from the inner surface from the signals generated responsive to the waves that have been reflected from the outer surface.

17. Apparatus according to claim 16, wherein the circuitry is operative to determine a thickness of the wall responsive to the signals generated by the waves that have been reflected from the inner surface and the waves that have been reflected from the outer surface.

18. Apparatus according to claim 1, and comprising one or more electrodes disposed on the distal portion of the probe, which are adapted to convey electrical signals to the circuitry responsive to electrical activity in the cavity, wherein the circuitry is adapted, responsive to the signals from the electrodes, to superimpose an indication of the electrical activity on the three-dimensional shape of the surface.

19. Apparatus according to claim 18, wherein the indication of the electrical activity comprises a map of electrical potentials at the surface of the cavity, which is registered with the three-dimensional shape of the surface.

20. Apparatus according to claim 1, and comprising a plurality of reference transducers outside the body, which are adapted to transmit acoustic waves into the body, such that the waves are received by the secondary acoustic transducers on the probe, causing the secondary acoustic transducers to generate electrical reference signals, and wherein the circuitry is adapted to process the reference signals so as to determine position coordinates of the probe.

21. Apparatus according to claim 20, wherein responsive to the determined position coordinates, the circuitry is adapted to define a position of the three-dimensional shape within the body.

22. Apparatus according to claim 1, and comprising one or more electrodes disposed on the distal portion of the probe, which are adapted to detect electrical activity in the cavity.

23. Apparatus according claim 22, wherein the one or more electrodes are adapted to detect varying electrical potentials at the surface of the cavity.

24. Apparatus according to claim 23, wherein the one or more electrodes comprise an array of non-contact electrodes, which are adapted to detect the varying electrical potentials at the surface, substantially without making contact with the surface.

25. A method for mapping a surface of a cavity within a body of a subject, comprising:

inserting a probe into the cavity, the probe having a longitudinal axis;

emitting acoustic waves within the cavity from a primary point on the probe;

receiving the acoustic waves at each of a plurality of secondary points distributed along the longitudinal axis of the probe, following reflection of the emitted waves from the surface of the cavity;

analyzing the received waves to determine times of flight of the waves;

reconstructing a three-dimensional shape of the surface of the cavity based on the determined times of flight, by determining, responsive to the times of flight, distances from the secondary points to corresponding points on the surface of the cavity generally opposite the secondary points, and combining the determined distances so as to reconstruct the shape, and distinguishing the waves received at the secondary points after one reflection from the surface of the cavity from the waves received after multiple reflections, and rejecting the waves received after the multiple reflections.

26. A method according to claim 25, wherein emitting the acoustic waves comprises emitting the waves in a phased array mode.

27. A method according to claim 25, wherein emitting the acoustic waves comprises emitting the waves in a non-phased array mode.

28. A method according to claim 25, wherein receiving the acoustic waves at the secondary points comprises receiving the acoustic waves by non-phased array ultrasound transducers.

29. A method according to claim 25, wherein inserting the probe into the cavity comprises inserting an intracardiac catheter into a chamber of the heart of the subject.

30. A method according to claim 25, wherein emitting and receiving the waves comprise emitting and receiving the waves while the probe is held substantially stationary at a single location in the cavity, and wherein reconstructing the three-dimensional shape comprises reconstructing the shape based substantially only on the waves received at the single location.

31. A method according to claim 25, and comprising determining position coordinates of the probe inside the body, wherein reconstructing the three-dimensional shape comprises reconstructing the shape responsive to the coordinates.

32. A method according to claim 31, wherein reconstructing the shape comprises defining a position of the shape inside the body using the coordinates.

33. A method according to claim 31, wherein emitting and receiving the waves comprise emitting and receiving the waves at a plurality of different locations of the probe in the cavity, and wherein reconstructing the shape comprises reconstructing the shape based on the waves received at the different locations, using the coordinates of the probe determined at the different locations.

34. A method according to claim 31, wherein determining the position coordinates comprises transmitting and receiving reference acoustic waves between reference points outside the body and the points on the probe, and analyzing the received reference waves to find distances between the reference points and the points on the probe, thus to determine the position coordinates.

35. A method according to claim 31, wherein determining the position coordinates comprises determining the coordinates using a position sensor in the probe.

36. A method according to claim 35, wherein determining the coordinates comprises detecting electrical current induced in a coil of the probe by an externally-applied magnetic field.

37. A method according to claim 25, wherein the cavity has a wall, and the surface comprises an inner surface of the wall and an outer surface of the wall, and wherein determining the distances comprises distinguishing the waves received at the secondary points after reflection from the inner surface from the waves received after reflection from the outer surface.

38. A method according to claim 37, wherein reconstructing the shape comprises determining a thickness of the wall by comparing the times of flight of the waves received after reflection from the inner surface to those of the waves received after reflection from the outer surface.

39. A method according to claim 25, and comprising analyzing the received waves to detect a spectral shift therein, so as to determine, responsive to the spectral shift, a velocity of motion of the surface.

40. A method according to claim 39, wherein reconstructing the shape comprises generating a map of the cavity that includes an indication of the velocity of motion of different areas of the surface.

41. A method according to claim 25, and comprising sensing electrical activity in the cavity using electrical sensors on the probe.

42. A method according to claim 41, wherein sensing the electrical activity comprises detecting varying electrical potentials at the surface of the cavity substantially without contact between the electrical sensors on the probe and the surface.

43. A method according to claim 41, wherein reconstructing the shape comprises superimposing an indication of the electrical activity on the reconstructed three-dimensional shape of the surface.

44. A method according to claim 43, wherein superimposing the indication of the electrical activity comprises generating a map of electrical potentials at the surface of the cavity, and registering the map with the three-dimensional shape of the surface.

* * * * *